United States Patent [19]
Ronan et al.

[11] Patent Number: 5,184,016
[45] Date of Patent: Feb. 2, 1993

[54] GLOW DISCHARGE SPECTROMETRY

[75] Inventors: Gerard A. Ronan, Manchester; Alistair Cole, Chester, both of England

[73] Assignee: VG Instruments Group Limited, Uxbridge, England

[21] Appl. No.: 639,802

[22] Filed: Jan. 10, 1991

[30] Foreign Application Priority Data

Jan. 10, 1990 [GB] United Kingdom ............... 9000547

[51] Int. Cl.$^5$ ........................ H01J 37/08; H01J 49/26
[52] U.S. Cl. .................................. 250/288; 250/423 R
[58] Field of Search ........... 250/281, 288, 282, 423 R; 313/359.1

[56] References Cited

U.S. PATENT DOCUMENTS

| | | |
|---|---|---|
| 3,543,077 | 11/1970 | Grimm . |
| 3,809,479 | 5/1974 | Whelan ............................. 250/307 |
| 4,446,403 | 5/1984 | Cuomo et al. . |
| 4,733,130 | 3/1988 | Miyama et al. .................. 313/619 |
| 4,812,040 | 3/1989 | Marcus et al. ................... 250/288 |
| 4,841,197 | 6/1989 | Takayama et al. . |
| 4,853,539 | 8/1989 | Hall et al. ........................ 250/281 |
| 4,912,324 | 3/1990 | Clark et al. ...................... 250/281 |
| 4,918,307 | 4/1990 | Shibata ............................. 250/288 |
| 4,955,717 | 9/1990 | Henderson ....................... 250/288 |

FOREIGN PATENT DOCUMENTS

| | | |
|---|---|---|
| 0174505 | 8/1985 | European Pat. Off. . |
| 0249424 | 8/1987 | European Pat. Off. . |
| 0297548 | 6/1988 | European Pat. Off. . |
| 1189847 | 1/1988 | Japan . |
| 972191 | 3/1961 | United Kingdom . |
| 2216335 | 2/1989 | United Kingdom . |
| 8706341 | 10/1987 | World Int. Prop. O. . |

OTHER PUBLICATIONS

Harrison, Hess, Marcus, King, *Glow Discharge Mass Spectrometry*, Anal. Chem. 1986 58 (2) pp. 341A-356A.
Wallace, et al. *Sensitivity and Cathode Geometry of the Hollow Cathode Ion. Ionization Source*, Anal. Chem. 1976 vol. 48 (1) pp. 118-120.
Mattson, et al., *Coaxial Cathode Ion Source for Solids Mass Spectrometry*, Anal. Chem. 1976 vol. 48 (3) pp. 489-491.
Bruhn, et al., *Simplified Solids Mass Spectrometer Combining a Glow Discharge Source with A Quadruple Mass Filter*, Anal. Chem. 1978 vol. 50 (2) pp. 373-375.
Jakubowski, et al., *Improvement of Ion Source Performance in Glow Discharge Mass Spectrometry*, Int. J. MS & Ion Proc. 1986 vol. 71 pp. 183-197.
Howorka, et al., *Ion Sampling From the Negative Glow Plasma in a Cylindrical Hollow Cathode*, Int. J. MS & Ion Phys. 1973 vol. 12 pp. 67-77.
Wronski, *A special glow discharge source of positive ions*, Vacuum, 1985 vol. 35 (7) 271-275.
Coburn et al., *Plasma Sources in Analytical Mass Spectrometry*, Appld. Spectrosc. Rev. 1981 vol. 17 (1) pp. 95-164.

Primary Examiner—Bruce C. Anderson
Attorney, Agent, or Firm—Merchant & Gould, Smith, Edell, Welter & Schmidt

[57] ABSTRACT

The invention provides glow discharge optical or mass spectrometers wherein a solid sample may be mounted in a unitary source assembly adjacent to a first electrode means. A second electrode means, spaced from sample by an insulating washer, is also part of the source assembly and engages with a discharge chamber into which a discharge gas is introduced. A glow discharge is maintained in the discharge by a potential differential difference applied between the first and second electrode means. In a mass spectrometer, ions formed in the discharge pass to a mass analyzer, while in an optical spectrometer, optical radiation form the discharge is spectroscopically analyzed. Particularly in the case of a mass spectrometer, the source assembly may be mounted on an insertion probe allowing it to be easily withdrawn from the vacuum envelope to facilitate sample changing and maintenance.

23 Claims, 3 Drawing Sheets

GLOW DISCHARGE SPECTROMETRY

This invention relates to various spectrometers and methods of spectrometry for the analysis of a solid sample wherein ions or other excited species are formed from the sample by the action of a glow discharge, and wherein either the ions are analyzed by mass spectrometry or the excited species are analyzed by optical spectroscopy.

The elemental composition of a solid sample may be analyzed by making the sample one electrode of a glow discharge established in a gas such as argon maintained at a sub-atmospheric pressure. Preferably a DC discharge is employed, in which case the sample is made the cathode, but a discharge sustained by some other means such as by applying an RF potential between the sample and another electrode may also be used. Energetic positive ions generated in the discharge are accelerated towards the cathode sample and strike it with sufficient energy to sputter material from it. This material, comprising atoms characteristic of the sample, enters the region of negative glow where it is ionized, or is excited to emit photons. The ions so produced may be extracted from the discharge and subsequently mass analyzed (see, e.g., Harrison. Hess, Marcus and King, Analytical Chemistry, 1986, vol 58 (2) pp 341A–356A), or the emission spectrum produced by the excited species may be analyzed with a suitable emission spectrometer. Both techniques employ very similar types of source, which typically comprises a chamber into which argon is introduced at a pressure of 0.001–10 torr and a cathode electrode, typically disposed at one end of the chamber, which comprises the sample. A glow discharge is established in the chamber between the sample (cathode) and another electrode (anode), by maintaining a suitable potential difference between them. For use with a mass spectrometer the chamber is provided with a small aperture through which ions can be extracted, and the chamber is disposed in the source vacuum envelope of the spectrometer so that it is evacuated through the ion-extraction aperture. For use with an optical emission spectrometer the source is provided with a window or lens in place of the ion-extraction aperture, and the chamber is completely sealed except for the gas inlet and an additional pumping port to which a small vacuum pump is connected. The term "optical" is used throughout to include both ultra-violet and infra-red radiation, as well as visible light.

Examples of prior glow discharge sources for use in the spectrometry of solids are described by J R Wallace et al in Analytical Chemistry 1976, vol 48 (1), pp 118–120; W A Mattson et al in Analytical Chemistry 1976, vol 48 (3) pp 489–491; C G Bruhn et al in Analytical Chemistry 1978, Vol 50 (2), pp 372–375; N Jakubowski et al in the International Journal of Mass Spectrometry and Ion Processes 1986, 71, pp 183–197; U.S. Pat. Nos. 3,809,479, and 4,733,130; Japanese Patent Application Publication No 01-18947; European Patent Applications Nos 0174505 and 0249424; and UK Patent Application No 2216355.

It is an object of this invention to provide an improved glow discharge spectrometer for solid sample analysis. It is also an object to provide an improved source for a glow discharge spectrometer. Further objects are to provide an improved glow discharge mass spectrometer and an improved glow discharge optical spectrometer. It is also an object to provide improved methods of glow discharge spectrometry for solids analysis.

According to one aspect the invention provides a spectrometer for the analysis of a solid sample, said spectrometer comprising a discharge chamber into which a discharge gas may be introduced, means for maintaining a glow discharge in said discharge chamber adjacent to a said solid sample, and means for analyzing emission from said glow discharge which is characteristic of said solid sample, wherein there is also provided a unitary source assembly engagable with said discharge chamber and wherein:

a) said unitary source assembly comprises first electrode means against which a said solid sample may be mounted and second electrode means which are adapted to provide the engagement between said unitary source assembly and said discharge chamber;

b) said unitary source assembly is removable from engagement with said discharge chamber to facilitate introduction of a said solid sample; and c) said means for maintaining a glow discharge comprises means for maintaining a potential difference between said first and said second electrode means when said unitary source assembly is engaged with said discharge chamber.

Preferably the unitary source assembly comprises a hollow body, conveniently cylindrical, which may be part of the first electrode means. The body may be closed at one end by an apertured anode plate (comprising the second electrode means) which is spaced from the end of the body by an insulating washer or 'O'-ring, preferably made of PTFE. The anode plate is adapted to provide engagement with the discharge chamber, conveniently by means of a conical portion which may engage with a conical socket on the discharge chamber, thereby exposing the sample to the discharge gas in the discharge chamber at a pressure at which a glow discharge can be established.

Conveniently, the insulating washer extends to cover at least part of the surface of the anode plate inside the body so that an electrically conductive sample can be placed against it without making electrical contact with the anode plate. A spring-loaded plunger may be provided inside the body to urge the sample against the insulating washer, and that plunger may make electrical connection to the sample so that the plunger, spring and body comprises the first electrode means. The discharge chamber and the anode plate may comprise the second electrode means. A glow discharge may then be formed in the discharge chamber adjacent to the sample (which is exposed to it through the aperture in the anode plate), so that the sample may be analyzed by glow discharge mass spectrometry or optical spectrometry.

In further preferred embodiments, means are provided for introducing and removing the unitary source assembly from engagement the discharge chamber to facilitate mounting a sample in it. In the case of a mass spectrometer the source assembly can be withdrawn from the spectrometer without admitting air into the housing. Alternatively, in the case of an optical spectrometer, a door or shutter may be provided.

In an alternative construction the body of the unitary source assembly may be part of the second electrode means which engages with the discharge chamber, and the first electrode means, including the sample, may be insulated from the body.

As in the case of prior glow discharge spectrometers, spectrometers according to the invention are preferably operated with a DC glow discharge in an inert discharge gas such as argon at a pressure between 0.001 and 10 torr. A potential difference of about 1 KV is typically applied between the first and second electrode means to maintain the discharge. However, a discharge sustained by an RF potential source may also be employed.

A preferred embodiment of the unitary source assembly comprises a cylindrical body closed at the end remote from the anode plate by an easily removable cap attached to the body by a bayonet catch or screw thread. The cap provides a surface against which the spring-loaded plunger may act to urge the sample against the insulated washer. Such an arrangement facilitates sample changing.

The invention may also be used with electrically insulating samples if the first electrode means comprises an auxiliary apertured disc electrode sandwiched between the insulated washer and the sample. In the case of either conductive or non-conductive samples, electrical connection to the first electrode means (usually the body of the unitary source assembly) is conveniently made through a sliding contact which connects with the source when it is engaged with the discharge chamber.

In another embodiment suitable for use with a sample in the form of a pin or rod, a unitary source assembly may comprise a hollow insulating body supported on a mounting flange which may be attached to the shaft of an insertion probe by an insulated coupling. An electrically conductive chuck is attacked inside the body to the flange and comprises a socket into which a pin sample can be inserted an secured with a locking screw. An insulating element comprising an aperture through which the sample may extend is sandwiched between the chuck and an anode plate (the second electrode means) which is attached to the insulating body and is adapted to engage the discharge chamber.

The invention further provides a glow discharge mass spectrometer incorporating an ion source substantially as described and arranged so that the unitary source assembly may be withdrawn on an insertion probe from the vacuum envelope of the spectrometer to facilitate sample changing and cleaning. In such a mass spectrometer the discharge chamber may comprise a hollow cylinder maintained at the accelerating potential of the spectrometer and adapted at one end to engage the second electrode means of the unitary source assembly. An inlet pipe may be provided to introduce a discharge gas into the chamber and a second port on the chamber may be connected to a small vacuum pump so that a flow of gas is maintained through the discharge chamber at the pressure most suitable for maintaining the required glow discharge. An aperture is provided in the end wall of the discharge cylinder opposite to the source assembly and axially aligned with the aperture in the anode plate through which ions characteristic of the sample may pass into a mass analyzer, which may be either a quadrupole or a magnetic sector analyzer, preferably contained in a second compartment in the vacuum envelope which is maintained at a pressure of $10^{-4}$ torr or less. For optimum performance that end wall of the discharge chamber may comprise a skimmer cone so that a nozzle-skimmer interface is created between the high and low pressure parts of the vacuum envelope and the transmission of ions from the discharge into the mass analyzer is maximized. Transfer optics comprising one or more electrostatic lens elements may also be provided between the discharge chamber and the mass analyzer, particularly in the case of a quadrupole analyzer.

In an alternative preferred embodiment the invention provides an optical emission spectrometer comprising an optical spectral analyzer, in which the discharge chamber is evacuated through one or more pumping apertures and is provided with a window through which at least some radiation emitted from the glow discharge may pass to the analyzer.

In further preferred embodiments the spectrometer also comprises means for storing a plurality of samples for sequential analysis, such as in a plurality of unitary source assemblies in a magazine, with a feeder provided for feeding the sources to and from the insertion probe.

The invention further provides a method for the spectrometric analysis of a solid sample comprising maintaining a glow discharge in a discharge gas contained in a discharge chamber and adjacent to said sample, and spectrometrically analyzing emission from said discharge which is characteristic of said sample, said method further comprising the steps of:

a) mounting a said sample against a first electrode means in a unitary source assembly which also comprises second electrode means adapted to engage with said discharge chamber;

b) moving said unitary source assembly to engage said second electrode means with said discharge chamber; and c) introducing said discharge gas into said discharge chamber and maintaining a potential difference between said first and said second electrode means to maintain said glow discharge;

and wherein said unitary source assembly may be removed from engagement with said discharge chamber to facilitate mounting of a said sample.

Methods according to the invention may comprise mass analyzing ions characteristic of said sample that may be generated in the glow discharge by means of a quadrupole or a magnetic sector mass analyzer, or they may comprise spectrometrically analyzing the radiation (UV, visible or IR) characteristic of said sample which may be emitted by the discharge. Preferably the discharge chamber and the unitary source assembly for use in the methods are constructed as described above.

In the case of a mass spectrometric method of analysis, the method may further comprise mounting the unitary source assembly on an insertion probe and introducing it on the probe through a vacuum lock mounted on the vacuum envelope of the mass spectrometer (which contains the discharge chamber) to engage the second electrode means with the discharge chamber. The method may also comprise transmitting at least some of the ions formed in said glow discharge into a second compartment within the vacuum envelope maintained at a pressure of $10^{-4}$ torr or less and into a mass analyzer, at least the entrance aperture of which is contained within said second compartment.

In an alternative preferred embodiment the invention comprises evacuating the discharge chamber through one or more pumping apertures; collecting optical emissions from said glow discharge and analyzing those optical emissions; thereby providing a method for the optical spectrometric or spectroscopic analysis of the sample.

The invention extends to a unitary glow discharge source assembly comprising: a first electrode means, a hollow and substantially cylindrical body closed at one end by a substantially circular second electrode plate having an aperture; an insulating element disposed between said first electrode means and said second electrode plate, and means for positioning said sample in contact with said first electrode means and proximate to said aperture. Preferably the sample is spaced apart from the second electrode plate by means comprising said insulating element.

Preferred embodiments of the invention will now be described in greater detail by way of example and with reference to the accompanying figures in which.

Figure 1:
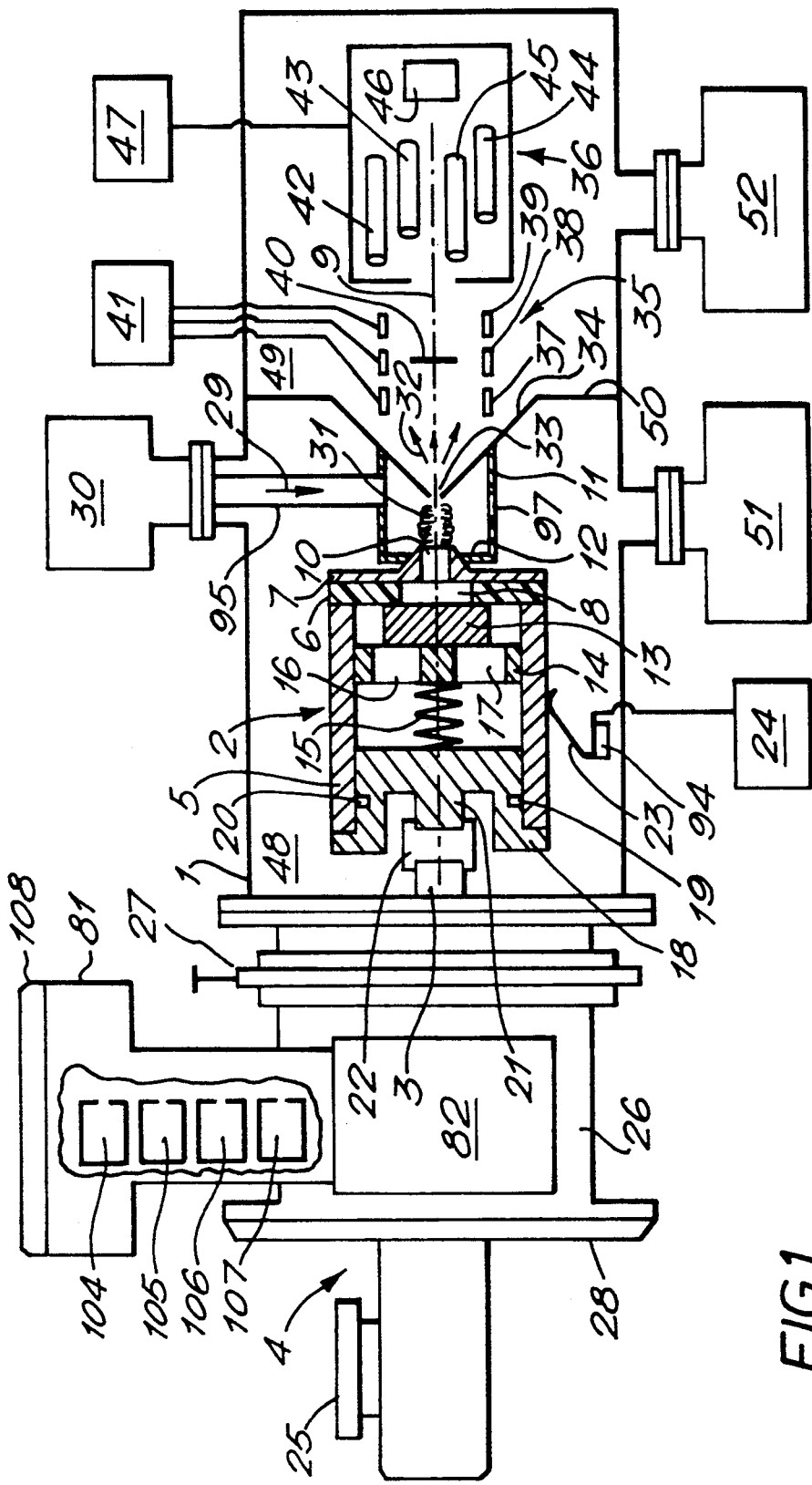
FIG. 1 is a schematic diagram of a mass spectrometer according to the invention.

Referring first to FIG. 1, a mass spectrometer comprises a vacuum envelope 1 for housing a removable unitary source assembly 2 which is mounted on a shaft 3 of an insertion probe mechanism 4. Discharge source 2 comprises a hollow and substantially cylindrical body 5 to which are fixed by means of insulated screws (not shown) a disc-shaped insulating washer 6 and a disc-shaped anode plate 7. The insulating washer 6 is made of PTFE and has a circular aperture 8 disposed on an axis 9 of source assembly 2 (which is also an axis of the mass spectrometer on which other components are aligned as shown). The anode plate 7 has a conical front portion comprising an aperture 10 aligned on axis 9. When the source assembly 2 is fully inserted into envelope 1 as shown, the conical portion of the anode plate 7 engages with a socket on the end wall 12 of the discharge chamber 11 so that electrical connection is made between the anode plate 7 via the discharge chamber 11, a skimmer cone 34 and the wall 50 to the vacuum envelope 1 to establish the anode plate 7 at ground potential.

A sample 13 is disposed within the body 5 and is held in compression against the insulating washer 6 by a disc-shaped plunger 14 which is urged against sample 13 by a spring 15. Holes 16 and 17 are formed in plunger 14 to reduce thermal conduction. Spring 15 is fixed on a locking ring 18 which locks onto the body 5 by a bayonet coupling comprising pegs 19 and 20. Locking ring 18 is linked via a coupling stud 21 and an electrically insulating block 22 to probe shaft 3. With source 2 inserted in the vacuum envelope 1, body 5 makes contact with a spring contact 23 (mounted on an insulating block 94) which is controlled at a negative potential, around −1 kV, by a power supply 24 which can deliver a current of around 10 mA. In this way it is arranged that source assembly 2 has a first electrode means comprising body 5, locking ring 18, spring 15, plunger 14 and sample 13, held at a cathode potential with respect to a second electrode means comprising anode plate 7 and the discharge chamber 11. Typical dimensions of components of source 2 are: diameter of body 5, 85 mm; thickness of the insulating washer 6, 0.5 mm; diameter of aperture 8 in washer 6, 15 mm; thickness of anode plate 7, 0.5 mm; and diameter of aperture 10 in anode 7, 5 mm. Apertures 8 and 10 are typically in respective ranges from 15 mm to 25 mm (washer), and 5 mm to 10 mm (anode), with the former greater than the latter by about at least 10 mm to substantially minimise contamination of the insulator by sputtered material. The source assembly and/or discharge chamber may further comprise additional electrodes or filaments for focussing ions or otherwise enhancing the glow discharge properties.

Inside vacuum envelope 1 the discharge chamber 11 has as its entrance aperture the aperture 10 in plate 7, and also has an exit aperture 33 formed in skimmer cone 34. Argon discharge gas 29 may be introduced into chamber 11 from a supply 30 via pipe 95. An outlet aperture 97 is also provided in chamber 11. To change a sample, or to otherwise maintain or service source assembly 2, firstly, insertion probe shaft 3 is operated by an actuator 25 to retract the source assembly 2 into a chamber 26. Then an isolation valve 27 is closed and chamber 26 is opened at a hinged door 28 to provide access to the source which may then be removed from shaft 3 and disassembled by uncoupling ring 18 from the body 5. Sample 13 may then be easily replaced, but additionally the insulating washer 6 may be replaced as may be necessary due to any build up of sputtered material, or any other deterioration from use. Also anode plate 7 may be replaced, for example with a plate having a different diameter aperture, if required. Thus one advantage of the invention is that, unlike in prior spectrometers, the insulating washer and anode plate can be readily withdrawn from the chamber in one conveniently maintainable assembly. The invention also allows the sample to be positioned controllably in elation to the other components of the source assembly while the assembly is outside of the vacuum envelope. Such repeatably controllable positioning gives improved reproducibility in analytical measurements. After maintenance, or the fitting of a sample, source assembly 2 is re-assembled by the locking ring 18 to body 5. It is then re-affixed to shaft 3, inserted into chamber 26, and with door 28 closed and valve 27 opened, is introduced to engage discharge chamber 11. In alternative embodiments the probe shaft could be omitted if preferred and the assembly may then be introduced to, or removed from, communication with chamber 1 merely by opening a flap, door or shutter. Also alternative means such as a further contact like contact 23 could be provided to set the potential of anode plate 7 if required. FIG. 1 shows a magazine 81 (having an entry lock 108) in which a plurality of source assemblies 104 to 107 (not drawn to scale), each like source 2 and containing a sample, may be stored for feeding sequentially to probe 4 by a feeder 82.

To analyse sample 13, argon discharge gas 29 is introduced to chamber 11 and a glow discharge 31 is struck between anode 7 and the cathode which comprises sample 13. Sample ions 32 pass from discharge 31 through aperture 33 and transfer optics 35 to a mass analyzer 36. The transfer optics 35 typically comprises a lens having three elements 37, 38 and 39 along with a stop 40 to prevent the line-of-sight passage of photons or neutral particles from the discharge to analyzer 36. A voltage controller 41 is provided to control ion optics 35. An energy filter (not shown) may also be provided to filter the sample ions before mass analysis. In this example analyzer 36 is a quadrupole analyzer comprising rods 42 to 45 together with an ion detector 46. Alternatively the spectrometer may comprise some other form of analyzer such as a magnetic sector analyzer which would require a different arrangement of the potentials applied to source 2 to ensure that the ions 32 are at an appropriate potential; i.e. the source would be floated at several kV with respect to the analyzer. A controller 47 is provided for analyzer 36 and processes data from detector 46 to produce a mass spectrum of the sample ions 32 from which the composition of sample 13 may be deduced.

The vacuum envelope 1 is essentially divided into two sub-compartments 48 and 49 by wall 50 and skimmer cone 34. A pump 51 maintains compartment 48 at between 0.001 torr and 10 torr as is suitable for maintaining the glow discharge. A further pump 52 maintains compartment 49 at a high vacuum of around $10^{-4}$ torr or lower.

While it is preferred, as described, for body 5 to be at first electrode (cathode) potential this is not essential to the invention and alternative embodiments may comprise a body case at some other potential such as second electrode (anode) potential, e.g. with a body continuous with and in electrical contact with the anode plate. In this case items such as locking ring 18 and plunger 14 would be insulated from the body case with electrical connection made to the sample (cathode) via shaft 3 (omitting insulator 22) for example.

Figure 2:
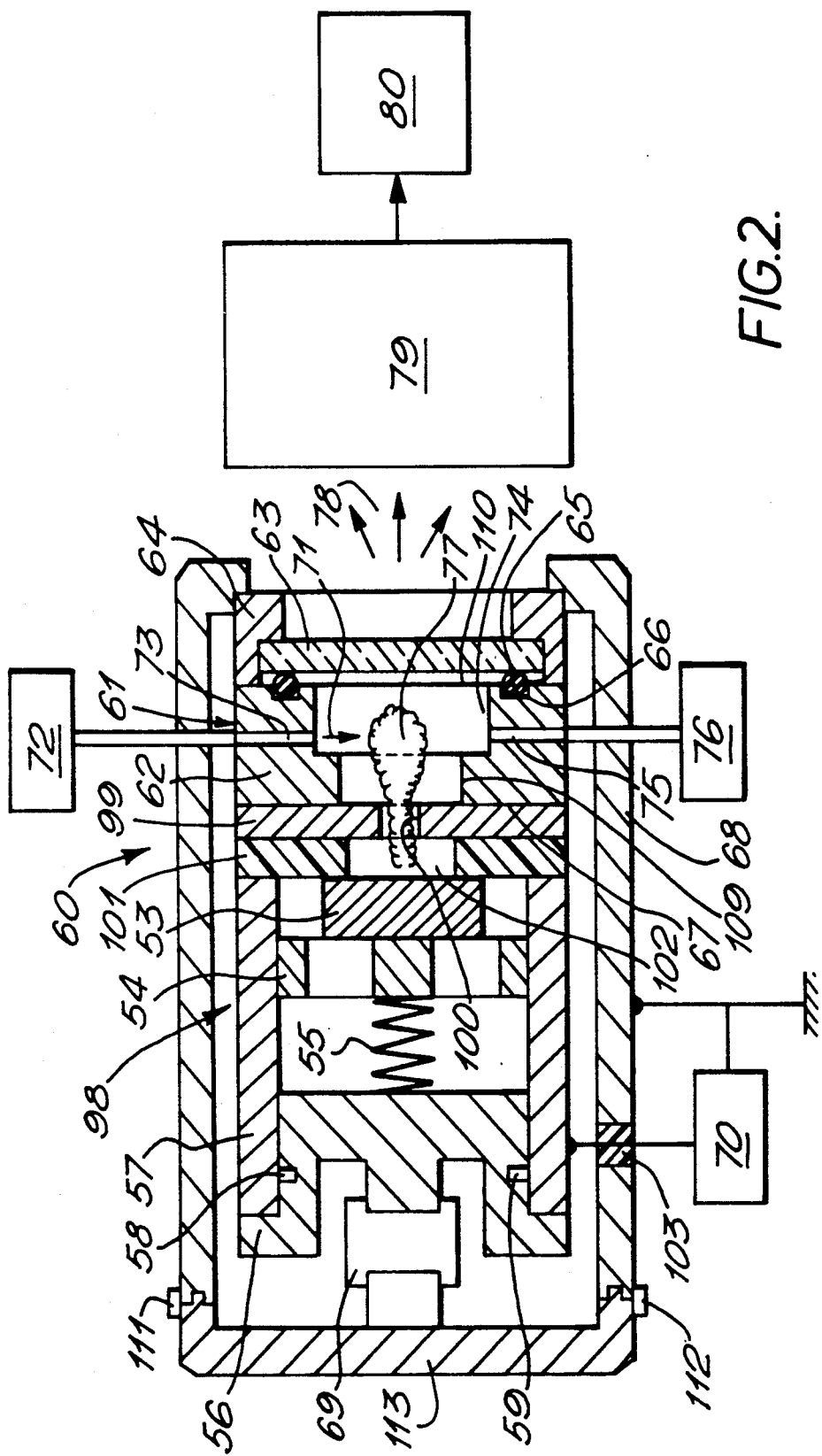
FIG. 2 is a schematic diagram of an optical emission spectrometer according to the invention.

Referring next to FIG. 2 an optical emission spectrometer comprises an emission cell 60 comprising a glow discharge source assembly 98 and a discharge chamber 61. The source assembly 98, like that of FIG. 1, comprises an anode plate 99 having an aperture 100, an insulator 101 having an aperture 102, a sample 53 urged against insulator 101 by a plunger 54 mounted on a spring 55, a locking ring 56 to which spring 55 is fixed and which is locked onto a substantially cylindrical casing 57 by a bayonet mechanism comprising pegs 58 and 59. Discharge chamber 61 comprises a substantially cylindrical body 62, defining an entrance aperture 109, an exit aperture 110 and a pumped cavity 74, to which a quartz window 63 is clamped by a clamping ring 64 and sealed by an O-ring 65 located in a groove 66. Anode plate 99 of source 98 is pressed against a face 67 of chamber body 62 by means of a clamp 68. In this way anode 99 is maintained at earth potential, while a power supply 70 maintains the other components of source 98 at a cathode potential, via an insulated connector 103; clamp 68 is insulated from the cathode potential by an insulating block 69. Argon gas 71 from a supply 72 is introduced to chamber 61 and source 98 through an inlet 73. The gas is removed from cavity 74 along an outlet 75 by a pump 76 which incorporates a gauge and flow restrictor for maintaining the cavity pressure typically in a range of from 1 torr to 10 torr. In operation a glow discharge 77 is struck in gas 71 between anode plate 99 and the cathode comprising sample 53. Optical emission 78 passing from discharge 77 through window 63 is analyzed by a spectral analyzer 79, the output of which is recorded by a data acquisition system 80. Maintenance of the spectrometer, to replace sample 53, or insulator 101, or anode plate 99, is effected by uncoupling clasps 111 and 112 in clamp 68 and withdrawing source 98 attached to a portion 113 of clamp 68, thereafter maintaining source 98 as described above for source 2. Automatic source changing and storage in a magazine may also be provided as for the earlier example. The apparatus of the optical spectrometer is generally simpler than the earlier example because of the less stringent vacuum requirements.

Figure 3:
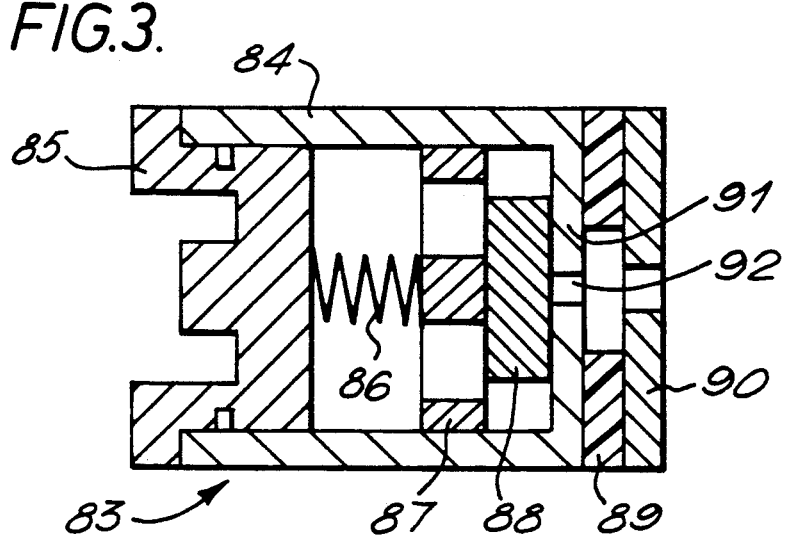
FIG. 3 shows a source assembly for a spectrometer according to the invention adapted for the analysis of non-conductive sample.

Referring next to FIG. 3 there is shown a unitary source assembly 83 similar to sources 2 and 48 described above but here adapted for the analysis of non-conductive samples.

Source 83 comprises a body 84, locking ring 85, spring 86, plunger 87, non-conductive sample 88, insulator 89 and anode plate 90. Body 84 has a conductive portion 91 approximately 0.25 mm thick (which could alternatively be formed from an additional plate) projecting as shown to define an aperture 92 having a diameter in the approximate range of from 1 mm to 6 mm, and typically equal to 2 mm. Body 84 with conductive portion 91, together with sample 88, forms a cathode electrode. Sample 88 is exposed through aperture 92 to a discharge struck between that cathode and anode 90.

Figure 4:
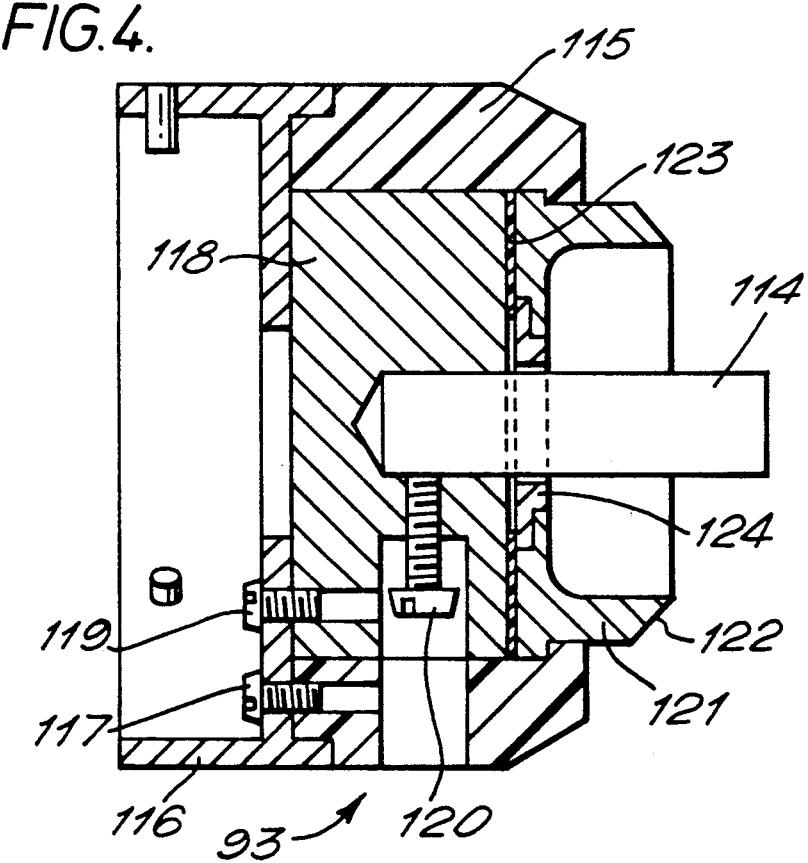
FIG. 4 shows a source assembly for a spectrometer according to the invention adapted for use with pin-shaped samples.

Referring next to FIG. 4, there is illustrated a unitary source assembly 93 in which a solid sample 114 in the form of a pin may be mounted. The assembly comprises a body 115 made of an insulating material which is secured to a bayonet flange 116 by screws 117. Flange 116 engages a part (not shown) similar to the locking ring 18 (FIG. 1) to enable the assembly 93 to be attached to an insertion probe. Inside the body 115 is a metallic chuck 118, secured to the flange 116 by screws 119, which contains a socket for the sample 114. A screw 120 is used to secure the sample 114 into the socket in the chuck 118.

An anode plate 121 comprising a taper 122 for engaging with the discharge chamber 11 and an insulating washer 123 are secured as shown by the body 115 against the face of the chuck 118. In order to prolong the life of the plate 121 the centre portion is formed by a tantalum mask 124 which contains a clearance hole through the pin sample 114 may protrude without making electrical contact with the plate 121.

When the source assembly 93 is engaged with the discharge chamber 11, the bayonet flange 116 and chuck 118 form the first electrode means and the anode plate 121 and mask 124 form the second electrode means of the invention.

The invention provides a spectrometer in one of several embodiments, not limited to the examples given above, which gives improved performance particularly in terms of reproducibility of measurements compared to prior spectrometers, which is especially advantageous in quantitative analyses. The invention also has the advantage of being more easily maintained, particularly for replacing an anode to cathode insulator or other source components, than prior spectrometers and provides a convenient means for sample changing which is suitable for automated batch processing if required.

We claim:

1. A spectrometer for the analysis of a solid sample, said spectrometer comprising a discharge chamber into which a discharge gas may be introduced, means for maintaining a glow discharge in said discharge chamber adjacent to a said solid sample, and means for analyzing emission from said glow discharge which is characteristic of said solid sample, wherein there is also provided a unitary source assembly engagable with said discharge chamber and wherein:
    a) said unitary source assembly comprises first electrode means against which a said solid sample may be mounted and second electrode means which provide the engagement between said unitary source assembly and said discharge chamber;
    b) said unitary source assembly is removable from engagement with said discharge chamber to facilitate introduction of a said solid sample; and c) said means for maintaining a glow discharge comprises means for maintaining a potential difference between said first and said second electrode means when said unitary source assembly is engaged with said discharge chamber.

2. A spectrometer as claimed in claim 1 wherein said unitary source assembly comprises a hollow substantially cylindrical body comprising part of said first electrode means which is closed at one end by an apertured anode plate spaced from it by an insulating washer, and wherein said anode plate comprises at least a part of said second electrode means and engages said discharge chamber.

3. A spectrometer as claimed in claim 2 wherein said insulating washer extends to cover at least a part of said anode plate inside said body, and a said sample is maintained in contact with said washer so as to cover at least a part of said aperture by spring means acting between a removable end cap which closes said body at the end remote from said anode plate and a plunger located behind said sample.

4. A spectrometer as claimed in claim 3 suitable for use with a non-conducting sample further comprising an auxiliary electrode disposed adjacent to said sample and comprising an aperture through which at least a part of said sample is exposed to the glow discharge.

5. A spectrometer as claimed in claim 2 suitable for use with a non-conducting sample further comprising an auxiliary electrode disposed adjacent to said sample and comprising an aperture though which at least a part of said sample is exposed to the glow discharge.

6. A spectrometer as claimed in claim 2 wherein said discharge chamber and a mass analyzer are disposed in a vacuum envelope, and said unitary source assembly is removably mounted on an insertion probe which enters said vacuum envelope through a vacuum lock, whereby said source assembly can be withdrawn on said probe through said vacuum lock to facilitate changing a said sample without admitting air into said vacuum housing.

7. A mass spectrometer as claimed in claim 6 wherein said discharge chamber comprises a hollow cylinder maintained at the accelerating potential of the mass analyzer, said chamber engaging at one end the second electrode means of the unitary source assembly and at the other end comprising a skimmer cone having a hole in its apex through which ions characteristic of a said sample generated in said glow discharge may pass from said discharge chamber to a compartment maintained at a pressure of less than $10^{-4}$ torr in which there is disposed at least the entrance aperture of said mass analyzer.

8. A glow discharge optical emission spectrometer as claimed in claim 2 wherein said discharge chamber is evacuated through one or more pumping apertures and is provided with a window through which at least some radiation emitted from the glow discharge may pass to an analyzer.

9. A glow discharge spectrometer as claimed in claim 2 wherein the pressure in said discharge chamber is maintained between 0.001 and 10 torr, said discharge gas is an inert gas such as argon, and a direct potential difference is applied between said first and second electrode means in order to establish said glow discharge.

10. A spectrometer as claimed in claim 1 wherein said unitary source assembly comprises a hollow insulated body supported on a mounting flange and wherein the following components are disposed in sequence from within said hollow body to said discharge chamber:

a) an electrically conductive chuck comprising a socket for receiving a said sample;
b) an insulating washer comprising an aperture through which said sample may extend; and
c) an anode plate engaging said discharge chamber and comprising an aperture through which said sample may extend without making contact with said plate;

and wherein said mounting flange and chuck comprise at least a part of said first electrode means and said anode plate comprises at least a part of said second electrode means.

11. A mass spectrometer as claimed in claim 10 wherein said discharge chamber and a mass analyzer are disposed in a vacuum envelope, and said unitary source assembly is removably mounted on an insertion probe which enters said vacuum envelope through a vacuum lock, whereby said source assembly can be withdrawn on said probe through said vacuum lock to facilitate changing a said sample without admitting air into said vacuum housing.

12. A glow discharge spectrometer as claimed in claim 10 wherein the pressure in said discharge chamber is maintained between 0.001 and 10 torr, said discharge gas is an inert gas such as argon, and a direct potential difference is applied between said first and second electrode means in order to establish said glow discharge.

13. A mass spectrometer as claimed in claim 1 wherein said discharge chamber and a mass analyzer are disposed in a vacuum envelope, and said unitary source assembly is removably mounted on an insertion probe which enters said vacuum envelope through a vacuum lock, whereby said source assembly can be withdrawn on said probe through said vacuum lock to facilitate changing a said sample without admitting air into said vacuum housing.

14. A mass spectrometer as claimed in claim 12 wherein said discharge chamber comprises a hollow cylinder maintained at the accelerating potential of the mass analyzer, said chamber engaging at one end the second electrode means of the unitary source assembly and at the other end comprising a skimmer cone having a hole in its apex through which ions characteristic of a said sample generated in said glow discharge may pass from said discharge chamber to a compartment maintained at a pressure of less than $10^{-4}$ torr in which there is disposed at least the entrance aperture of said mass analyzer.

15. A glow discharge optical emission spectrometer as claimed in claim 1 wherein said discharge chamber is evacuated through one or more pumping apertures and is provided with a window through which at least some radiation emitted from the glow discharge may pass to an analyzer.

16. A glow discharge spectrometer as claimed in claim 1 wherein the pressure in said discharge chamber is maintained between 0.001 and 10 torr, said discharge gas is an inert gas such as argon, and a direct potential difference is applied between said first and second electrode means in order to establish said glow discharge.

17. A method for the spectrometric analysis of a solid sample comprising maintaining a glow discharge in a discharge gas contained in a discharge chamber and adjacent to said sample, and spectrometrically analyzing emission from said discharge which is characteristic of said sample, said method further comprising the steps of:

a) mounting a said sample against a first electrode means in a unitary source assembly which also comprises second electrode means engaging with said discharge chamber;

b) moving said unitary source assembly to engage said second electrode means with said discharge chamber; and c) introducing said discharge gas into said discharge chamber and maintaining a potential difference between said first and said second electrode means to maintain said glow discharge;

and wherein said unitary source assembly may be removed from engagement with said discharge chamber to facilitate mounting of a said sample.

18. A method of mass spectrometry as claimed in claim 17 wherein ions characteristic of a said sample are generated in said glow discharge and are transmitted from said discharge chamber to a mass analyzer.

19. A method of mass spectrometry as claimed in claim 18 which further comprises mounting said unitary source assembly ion an insertion probe and introducing it on said probe through a vacuum lock mounted on a vacuum envelope in which said discharge chamber and said mass analyzer are disposed to engage said second electrode means with said discharge chamber.

20. A method of spectrometry as claimed in claim 18 wherein said discharge gas comprises argon and said glow discharge is maintained by application of a direct potential difference between said first and said second electrode means.

21. A method of optical spectrometry as claimed in claim 17 wherein optical radiation characteristic of a said sample emitted by said glow discharge is analyzed by an optical spectrometer.

22. A method of spectrometry as claimed in claim 21 wherein said discharge gas comprises argon and said glow discharge is maintained by application of a direct potential difference between said first and said second electrode means.

23. A method of spectrometry as claimed in claim 17 wherein said discharge gas comprises argon and said glow discharge is maintained by application of a direct potential difference between said first and said second electrode means.

* * * * *

UNITED STATES PATENT AND TRADEMARK OFFICE
CERTIFICATE OF CORRECTION

PATENT NO. : 5,184,016
DATED : February 2, 1993
INVENTOR(S) : Ronan et al It is certified that error appears in the above-identified patent and that said Letters Patent is hereby corrected as shown below:

On the title page, item [57]

Abstract, line 9, after the word "discharge" insert --chamber--.

Abstract, line 13, "form" should be --from--

Column 3, line 5, "1 KV" should be --1kV--.

Column 6, lines 31, "elation" should be --relation--.

Column 6, line 43, "1" should be --11--.

Column 9, line 30, "though" should be --through--

Signed and Sealed this

First Day of July, 1997

Attest:

BRUCE LEHMAN

*Attesting Officer*  *Commissioner of Patents and Trademarks*